United States Patent
Uchida et al.

(10) Patent No.: US 6,939,858 B2
(45) Date of Patent: Sep. 6, 2005

(54) MALTO-OLIGOSACCHARIDE DERIVATIVES AND USE THEREOF

(75) Inventors: Riichiro Uchida, Noda (JP); Ayako Nasu, Noda (JP)

(73) Assignee: Kikkoman Corporation (JP)

( * ) Notice: Subject to any disclaimer, the term of this patent is extended or adjusted under 35 U.S.C. 154(b) by 210 days.

(21) Appl. No.: 10/297,408

(22) PCT Filed: Jun. 1, 2001

(86) PCT No.: PCT/JP01/04653

§ 371 (c)(1),
(2), (4) Date: Dec. 6, 2002

(87) PCT Pub. No.: WO01/94367

PCT Pub. Date: Dec. 13, 2001

(65) Prior Publication Data

US 2004/0006046 A1 Jan. 8, 2004

(30) Foreign Application Priority Data

Jun. 6, 2000 (JP) .................................... 2000-168363

(51) Int. Cl.$^7$ ................................. A61K 31/70; C07H 17/00
(52) U.S. Cl. ............................. 514/25; 514/53; 514/54; 536/17.3; 536/17.4; 536/123.1
(58) Field of Search ......................... 514/25, 53, 54, 514/26; 536/17.3, 17.4, 123.1

(56) References Cited

FOREIGN PATENT DOCUMENTS

GB         2 064 527         6/1981
WO         WO 00/50434       8/2000

OTHER PUBLICATIONS

Agricultural and Biological Chemistry, vol. 50, 639–644, 1986, Motoo Arai et al,.

*Primary Examiner*—Elli Peselev
(74) *Attorney, Agent, or Firm*—Banner & Witcoff, Ltd.

(57) ABSTRACT

The present invention provides a substance which strongly inhibits human α-amylase and is effective for the prevention and treatment of hyperglycemia, for example, diabetes and the diseases caused thereby, and an α-amylase inhibitor and a prophylactic or therapeutic agent for hyperglycemia containing the said substance as active principle.

Maltoligosaccharide derivatives represented by the following formula:

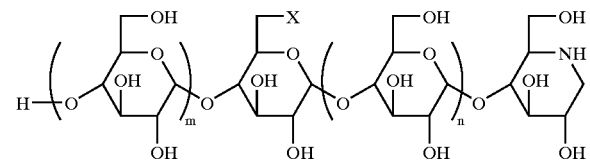

(wherein n is an integer of 0 to 2; m is an integer of 0 to 2; and X represents a hydrogen atom or a hydrophobic group) or their hydrates or physiologically acceptable salts are provided, and they are contained as active principle to prepare an α-amylase inhibitor and a prophylactic or therapeutic agent for hyperglycemia such as diabetes.

9 Claims, 1 Drawing Sheet

MALTO-OLIGOSACCHARIDE DERIVATIVES AND USE THEREOF

This is a U.S. national phase application under 35 U.S.C. § 371 of International Application No. PCT/JP01/04653, filed Jun. 1, 2001, which claims the benefit of priority of Japanese Application No. 2000-168363, filed Jun. 6, 2000.

TECHNICAL FIELD

The present invention relates to maltoligosaccharide derivatives having a specific structure, and their uses. More particularly, it relates to an α-amylase inhibitor and medicinal preparations useful for the prevention or treatment of hyperglycemia, for example diabetes and its complications, which contain the said derivatives as an active component.

BACKGROUND ART

Carbohydrates ingested by a mammal are initially digested (hydrolyzed) to some extent with salivary α-amylase in the mouth and stomach, and then digested wholly with pancreatic α-amylase in the duodenum and jejunum into an oligosaccharide or disaccharide. There are further hydrolyzed by glucoside-hydrases such as glucoamylase and maltase to finally become a monosaccharide such as glucose, which is absorbed up through the villi on the intestinal tract membranes. Thus, after ingestion of carbohydrates, there takes place a temporary rise of blood glucose level, or so-called hyperglycemia, due to the absorption of glucose. Normally, however, this temporarily elevated blood glucose level is adjusted to stay in a normal range by the homeostasis maintenance system in the living body to recover from hyperglycemia.

However, abnormalities of carbohydrate metabolism, such as long-time continuance of alimentary hyperglycemic symptoms or occurrence of an abnormally high blood glucose level, may lead to a disease called hyperglycemia, causing such cases as obesity and diabetes. This obesity is caused as secretion of a large volume of insulin is promoted by a hyperglycemic symptom induced by overeating, provoking an increase of synthesis of fat and a decrease of its decomposition to accumulate fat in the body. On the other hand, diabetes is caused as secretion of a large volume of insulin is promoted by a hyperglycemic symptom induced by overeating to provoke a reduction of sensitivity of insulin receptors or exhaustion of β cells of the islet of Langerhans in the pancreas. It is also known that obesity and diabetes tend to trigger many serious complications such as hyperlipidemia, hypertension, arteriosclerosis, autonomic troubles and cataract.

As the potent therapeutic agents for such hyperglycemia, there are clinically used the pharmaceuticals containing a digestive enzyme inhibitor, such as "Basen" containing Voglibose (produced by Takeda Pharmaceutical Industries Co., Ltd.) and "Glucobay" containing acarbose (produced by Bayer Ltd.). Both of these compounds, however, have the disadvantage of producing undesirable side effects, such as causing abdominal distention, meteorism, increased flatulence, loose passage, diarrhea or abdominal pain.

DISCLOSURE OF THE INVENTION

An object of the present invention is to provide a pharmaceutical substance which is free of the said disadvantages of the conventional therapeutic and prophylactic agents for hyperglycemia and is strongly inhibitive against human α-amylase and effective for the prevention and treatment of hyperglycemia, for example, diabetes and the diseases caused thereby, and an α-amylase inhibitor and a prophylactic or therapeutic agent for hyperglycemia containing the said substance as active principle.

As a result of strenuous studies for attaining the above object, the present inventors found that the maltoligosaccharide derivatives obtained by converting the reduced terminal glucose residue of oligosaccharides to deoxynojirimycin residue and converting the 6-position of the 2nd to 4th glucose residue (with the deoxynojirimycin residue being counted as the 1st) to a hydrophobic group, and their hydrates or physiologically acceptable salts (the said maltoligosaccharide derivatives and their hydrates or physiologically acceptable salts being hereinafter called representatively as "maltoligosaccharide derivatives") strongly inhibit α-amylases α-amylase derived from pancreatic juice and α-amylase derived from salivary gland; hereinafter, α-amylase derived from human pancreatic juice being referred to as HPA and α-amylase derived from human salivary gland being referred to as HSA) and retard digestion and absorption of glucose, and that by using these compounds as a therapeutic or prophylactic agent for hyperglycemia, it would be possible to overcome the said defects of the conventional technology. The present invention has been completed on the basis of these findings.

Thus, the present invention provides maltoligosaccharide derivatives represented by the following formula (1):

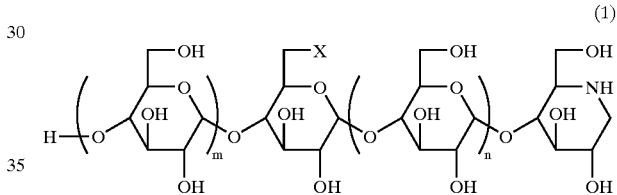

(wherein n is an integer of 0 to 2; m is an integer of 0 to 2; and X represents a hydrogen atom or a hydrophobic group).

The present invention also provides an α-amylase inhibitor containing said maltoligosaccharide derivative as an active component.

The present invention further provides a prophylactic or therapeutic agent for hyperglycemia containing said maltoligosaccharide derivative as an active component.

The present invention is described in detail below.

BEST MODE FOR CARRYING OUT THE INVENTION

The maltoligosaccharide derivatives of the present invention are represented by the above formula (1) in which n is an integer of 0 to 2, m is an integer of 0 to 2, and X represents a hydrogen atom or a hydrophobic group. As the said hydrophobic group, halogen atoms such as fluorine, chlorine, bromine and iodine, substituted or non-substituted alkyloxy group, substituted or non-substituted alkylthio group, substituted or non-substituted alkylsulfonyl group, substituted or non-substituted alkylcarbamoyl group, and azido group can be mentioned as preferred examples.

In use of the derivatives of the present invention as an α-amylase inhibitor or as a preventive or therapeutic agent for hyperglycemia, it is preferable for the reasons stated later that the said derivatives are those defined by the formula (1) wherein n is an integer of 0 to 2, m is an integer of 0 to 2 and X is a hydrogen atom or a hydrophobic group, or their hydrates or physiologically acceptable salts. It is especially preferable that n is 1, m is 0 to 1, and X is a hydrogen atom.

In producing the derivatives of the present invention represented by the formula (1), they can be efficiently synthesized by using, for instance, a maltoligosaccharide derivative represented by the following formula (2):

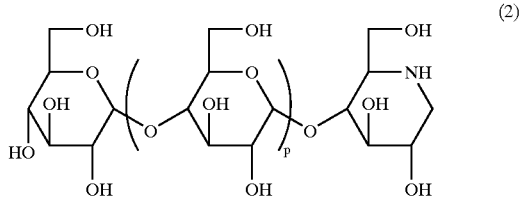

(2)

(wherein p is an integer of 0 to 4), that is, maltoligosyl-deoxynojirimycin as the starting material for the synthesis. This maltoligosaccharide derivative can be synthesized by coupling commercial deoxynojirimycin with starch by using a bacterial amylase, according to the method as described in, for example, Agricultural and Biological Chemistry, Vol. 50, 639-644, 1986. Alternatively, it can also be efficiently synthesized by coupling deoxynojirimycin with α-cyclodextrin by using cyclodextrin glucosyl transferase, and if necessary further acting glucoamylase.

The objective derivative of the present invention can be obtained as follows; by using as starting material maltoligosyl-deoxynojirimycin represented by the above formula (2), after protecting, if necessary, the cyclic amino group with, for instance, benzyl chloroformate, reacting it with p-toluenesulfonyl chloride (tosyl chloride) in, for instance, pyridine isolating if necessary 6-O-tosylmaltoligosyl-N-carbobenzoxydeoxynojirimycin by a conventional method, and reacting it with, for instance, sodium halide in N,N-dimethylformamide to obtain 6-halogenated maltoligosyl-N-carbobenzoxy-deoxynojirimycin. This 6-halogenated maltoligosyl-N-carbobenzoxydeoxynojirimycin may be deprotected by alkali treatment to give 6-halogenated maltoligosyl-deoxynojirimycin. Alternatively, 6-halogenated maltoligosyl-N-carbobenzoxydeoxynojirimycin is reduced by adding hydrogen gas in the presence of palladium carbon and if necessary subjected to alkali treatment to simultaneously reduce the 6-halogen group and deprotection in cyclic amino group, thereby obtaining 6-deoxymaltoligosyl-deoxynojirimycin.

Then the derivatives of the present invention obtained in the manner described above are subjected to a pertinent treatment by a conventional method, for example, precipitation using an appropriate organic solvent or column chromatography using an ion exchange resin, aminopropyl silica gel, silica gel, activated carbon or the like to obtain the objective purified derivatives of the present invention. For synthesizing derivatives of the present invention with m=1 or 2 preferentially, a compound with m=0 is previously synthesized, and it is coupled with α-cyclodextrin by using cyclodextrin glucosyl transferase and if necessary subjected to a glucoamylase reaction, whereby it is possible to efficiently synthesize the desired derivative.

Among the derivatives of the formula (1) of the present invention obtained in the manner described above, the maltoligosaccharide derivatives with X being a hydrophobic group such as hydrogen atom or halogen atom have a strong inhibitory activity against HPA and HSA as explained below. The derivatives of the present invention have approximately 5- to 9-fold higher amylase inhibitory activity than the compounds in which X is an unsubstituted group, i.e. an OH group. The compounds with unsubstituted X tend to be decomposed into glucosidases existing in the intestinal tracts and are therefore greatly lowered in the amylase inhibitory activity thereof. The derivatives of the present invention represented by the formula (1) are hardly decomposed in the intestinal tracts as X is modified, so that their activity lasts for a long time in the intestinal tracts, which consequently allows a reduction of dose in administration of the derivatives. In view of affinity with amylase, the group X is advantageously a hydrophobic group, particularly hydrogen atom. Also, for the reason of affinity with amylase, n is advantageously 0 to 2, especially 1, and m is also advantageously 0 to 2, especially 0 or 1.

As the derivatives of the present invention have a strong inhibitory activity against α-amylase as explained above, it is possible to use them as an α-amylase inhibitor as an active principle thereof. Also, since the derivatives of the present invention having such an inhibitory activity can inhibit carbohydrate metabolism of animals, they check the rise of blood glucose level and are effective as a prophylactic or therapeutic agent for hyperglycemia, for example, diabetes, obesity and other diseases caused thereby, such as hyperlipidemia, fatty liver, autonomic ataxia, arteriosclerosis, cataract, etc., particularly for diabetes.

The α-amylase inhibitor and the prophylactic or therapeutic agent for hyperglycemia according to the present invention can be used in the form of the derivatives of the present invention or their hydrates, or as any non-toxic salt obtained by reacting the derivatives of the present invention with a pharmacologically acceptable acid or base. As the said acid, inorganic acids such as hydrochloric acid, hydrobromic acid, sulfuric acid, phosphoric acid and nitric acid, and organic acids such as acetic acid, malic acid, citric acid, ascorbic acid, mandelic acid and methanesulfonic acid can be used. As the base, sodium hydroxide, potassium hydroxide, ammonium hydroxide, calcium hydroxide and the like can be used.

The α-amylase inhibitor and the prophylactic or therapeutic agent for hyperglycemia according to the present invention are prepared by containing the derivatives of the present invention either singly or if necessary by combining two or more of them as active principle. The α-amylase inhibitor and the prophylactic or therapeutic agent for hyperglycemia according to the present invention can be offered in various forms of preparation such as tablet, powder, granule, capsule, syrup, suppository, injection, drip infusion, etc., by using the derivatives of the present invention singly or as a concoction thereof with a compounding agent or agents such as excipient, lubricant, diluent, stabilizer, pH adjuster, antiseptic, sweetener, aromatic, taste corrective, colorant, preservative, emulsifier, binder, and basic material. Conventional methods can be used for the production of these preparations. As excipient, there can be used those commonly in use, such as potato starch, lactose, crystal cellulose and mannitol. As lubricant, magnesium stearate, talc, hardened oil and the like can be used. As sweetener, aromatic and taste corrective, it is possible to use, for example, common salt, saccharin, orange oil, citric acid, menthol, malic acid and the like.

The dosage of the α-amylase inhibitor, the prophylactic or therapeutic agent for hyperglycemia and the prophylactic or therapeutic agent for diabetes according to the present invention will vary with the way of administration, the particular condition being treated, the age and body weight of the patient, etc., but usually it is preferably selected from the ambit of 10 to 3,000 mg, more preferably 50 to 300 mg as the amount of the derivative of the present invention per day for adults.

The way of administration may be either oral or parenteral, but oral administration is advantageous. Beside the uses described above, the derivatives of the present invention, either alone or as a suitable combination with said compounding agents, may be added to foods, for example, coffee, soft drinks, fruit juices, jam, biscuits, etc., to provide health-keeping foods having an α-amylase inhibitory effect.

The present invention will be described in further detail by showing the examples thereof.

EXAMPLE 1

Preparation of O-(6-deoxy)-α-D-glucopyranosyl-(1→4)-O-(α-D-glucopyranosyl)-(1→4)-deoxynojirimycin (Herein-after Referred to as DOGGDN)

Maltosyl-deoxynojirimycin (hereinafter referred to as GGDN) (1.5 g, 3.1 mmol) represented by the following structural formula (3):

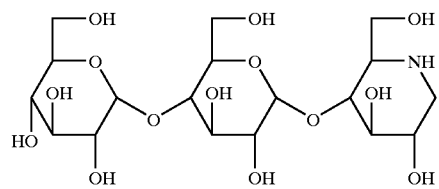

(3)

was dissolved in 40 ml of distilled water, to which sodium hydrogencarbonate (781 mg, 9.3 mmol) and benzyl chloroformate (1.0 g, 6.2 mmol) were added and reacted with stirring at room temperature for 7 hours. After the completion of the reaction, the reaction solution was applied to ODS chromatography ($H_2O$→10% ethanol, gradient) for purification and the fractions containing the objective compound was concentrated and lyophilized to obtain maltosyl-N-carbobenzoxydeoxynojirimycin (1.1 g, 1.8 mmol, 57%) having the following structural formula (4):

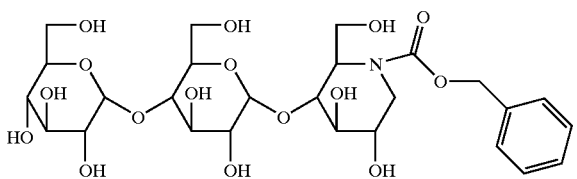

(4)

Then maltosyl-N-carbobenzoxydeoxynojirimycin (1.9 g, 3.1 mmol) obtained in the same way as described above was dissolved in 30 ml of pyridine, to which tosyl chloride (886 mg, 4.7 mmol) was added and the mixture was reacted under cooling with ice for 2 days. Nextly, 15 ml of distilled water was added to cease the reaction and the solution was evaporated to dryness. The residue was dissolved in a small quantity of distilled water, then this solution was applied to ODS chromatography ($H_2O$→50% ethanol, gradient) for purification and the fractions containing the objective compound was concentrated and lyophilized to obtain $6^2$-O-tosylmaltosyl-N-carbobenzoxydeoxynojirimycin (780 mg, 1.0 mmol, 32%) having the following structural formula (5) as a colorless powder:

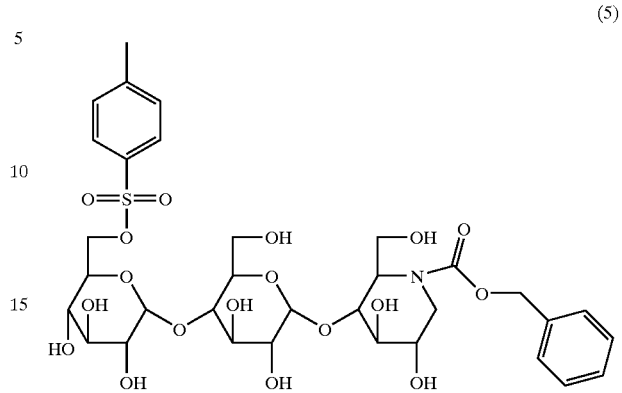

(5)

Then the obtained $6^2$-O-tosylmaltosyl-N-carbobenzoxydeoxynojirimycin (280 mg, 0.36 mmol) was dissolved in 30 ml of N,N-dimethylformamide, to which sodium iodide (500 mg, 3.3 mmol) was added and the mixture was stirred at 80° C. for 8 hours. After the completion of the reaction, the reaction solution was applied to ODS chromatography ($H_2O$→30% ethanol, gradient) for purification and the fractions containing the objective compound was concentrated and lyophilized to obtain $6^2$-iodomaltosyl-N-carbobenzoxydeoxynojirimycin (160 mg, 0.28 mmol, 78%) having the following structural formula (6) as a colorless powder:

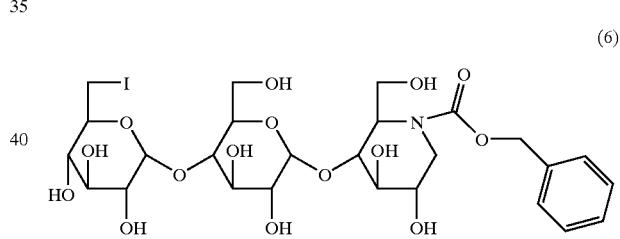

(6)

Then the obtained $6^2$-iodomaltosyl-N-carbobenzoxydeoxynojirimycin (100 mg, 0.14 mmol) was dissolved in 10 ml of distilled water, to which palladium/activated carbon (Pd 10%, 10 mg) was added, followed by the addition of hydrogen gas with stirring, and the mixture was reacted at room temperature for 16 hours. After the completion of the reaction, palladium/activated carbon was filtered off with Celite® and 2 ml of a 1N NaOH was added to the filtrate to carry on the reaction with stirring at 40° C. for 3 hours. After the completion of the reaction, the solution was neutralized with an 1N HCl and concentrated. The concentrated solution was applied to CG50 ion exchange resin ($NH_4^+$) column chromatography (eluted with $H_2O$) for purification and the fraction containing the objective compound was concentrated and lyophilized to obtain O-(6-deoxy-α-D-glucopyranosyl)-(1→4)-O-(α-D-glucopyranosyl)-(1→4)-deoxynojirimycin (60 mg, 0.13 mmol, 91%) having the following structural formula (7) as a colorless powder:

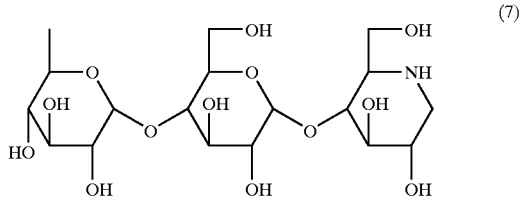

(7)

$^1$H-NMR (D$_2$O) δ: 1.29 (d, 3H, J=6.2 Hz, H-6c), 2.57 (dd, 1H, J=11.7 and 11.4 Hz, H-1a), 2.73–2.84 (m, 1H, H-5), 3.16 (dd, 1H, J=11.7 and 5.1 Hz, H-1a), 3.19 (t, 1H, J=8.4 Hz, H-4a), 3.51–4.02 (m), 5.35 (d, 2H, J=3.6 Hz, H-1b-c); $^{13}$C-NMR (D$_2$O) δ: 19.39 (—CH$_3$), 51.25 (C-5a), 102.7 and 102.9 (C-1b-c).

Anal. calcd. for C$_{18}$H$_{33}$NO$_{13}$·0.5H$_2$O: C, 45.00; H, 7.13; N, 2.92. Found: C, 44.95; H, 6.96; N, 3.00.

EXAMPLE 2

Preparation of O-(α-D-glucopyranosyl)-(1→4)-O-(6-deoxy-α-D-glucopyranosyl)-(1→4)-O-(α-D-glucopyranosyl)-(1→4)-deoxynojirimycin (Hereinafter Referred to as GDOGGDN)

DOGGDN (100 mg, 0.21 mmol) obtained in the same way as in Example 1 and 1 g of α-cyclodextrin were dissolved in 30 ml of a 10 mM phosphaste buffer (pH 7.0), to which cyclodextrin glucanotransferase (500 μl, produced by Amano Pharmaceutical Co., Ltd.) and the mixture was stirred at 37° C. for 8 hours. Then, the reaction solution was boiled at 100° C. for 30 minutes to cease the reaction. After cooling with ice, glucoamylase (200 mg, 1100 U produced by Kikkoman Corporation) was added to carry on the reaction for 6 hours. Then, the reaction solution was boiled at 100° C. for 30 minutes to cease the reaction. The reaction solution was filtered through Celite bed and concentrated. The concentrated solution was applied to CG50 ion exchange resin (NH$_4^+$) column chromatography (eluted with H$_2$O) for purification and the fraction containing the objective compound was concentrated and lyophilized to obtain O-(α-D-glucopyranosyl)-(1→4)-O-(6-deoxy-α-D-glucopyranosyl)-(1→4)-O-(α-D-glucopyranosyl)-(1→4)-deoxynojirimycin (70 mg, 0.11 mmol, 52%) having the following structural formula (8) as a colorless powder:

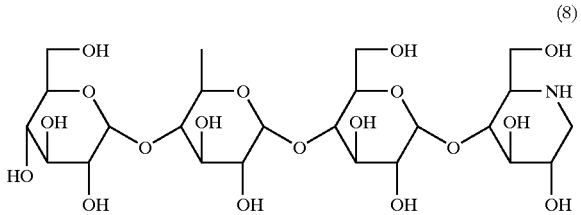

(8)

$^1$H-NMR (D$_2$O) δ: 1.28 (d, 3H, J=6.3 Hz, H-6c), 2.58 (dd, 1H, J=11.8 and 11.4 Hz, H-1a), 2.73–2.84 (m, 1H, H-5a), 3.16 (dd, 1H, J=11.7 and 5.1 Hz, H-1a), 3.19 (t, 1H, J=8.4 Hz, H-4a), 3.51–4.02 (m), 5.32~5.42 (m, 3H, H-1b-d); $^{13}$C-NMR (D$_2$O) δ: 19.40 (—CH$_3$), 51.26 (C-5a), 102.5, 102.8, and 102.9 (C-1b-d).

Anal. calcd. for C$_{24}$H$_{43}$NO$_{18}$H$_2$O: C, 44.24; H, 6.96; N, 2.15. Found: C, 44.12; H, 6.95; N, 2.21.

EXAMPLE 3
(Inhibition of Amylase Activity in Vitro Test)
(1) Preparation of Human α-Amylase Solution Purified water was added to commercial HPA and HSA to dissolve them to a concentration of 350 IU/1 to prepare an α-amylase solution. "Calibzyme·AMY" (produced by International Reagents Corp., Japan) was used as this commercial human α-amylase. The α-amylase activity was determined with reference to the calibration curves of a commercial α-amylase determining reagent "Neo·Amylase Test, Daiichi" (produced by Daiichi Pure Chemicals Co., Ltd., Japan).

(2) Preparation of Inhibitor Solutions

Using DOGGDN and GDOGGDN obtained in the same way as described in Examples 1 and 2, and GGDN which is a sample for comparison of activity, there were prepared the inhibitor solutions by dissolving the said compounds in purified water to a final concentration of 5 to 0.0001 mM.

(3) Determination of Human α-amylase Inhibiting Activity (IC$_{50}$) of the Inhibitor To 100 μl of the HPA or HSA solution were added 3.0 ml of purified water, 1.0 ml of inhibitor solution and one tablet of blue starch of "Neo·Amylase Test, Daiichi" (produced by Daiichi Pure Chemicals Co., Ltd., Japan). After stirring by a mixer for about 10 seconds, the mixture was warmed at 37° C. for 30 minutes and then further stirred by adding 1.0 ml of a 0.5 N sodium hydroxide solution to cease the reaction, after which the solution was centrifuged (1,500 G, 5 min.) and absorbance of the supernatant at 620 nm was measured. As a blank, purified water was used instead of the inhibitor solution. Results are shown in Table 1. "IC$_{50}$" signifies the final concentration (mM) of an inhibitor for reducing 50% of the activity of the HPA or HSA solution.

TABLE 1

| Inhibitor | IC$_{50}$ (mM) | |
| --- | --- | --- |
|  | HPA | HSA |
| GGDN (Comp. Example) | 0.26 | 0.26 |
| DOGGDN (Example) | 0.04 | 0.03 |
| GDOGGDN (Example) | 0.05 | 0.03 |

As is seen from Table 1, the maltoligosaccharide derivatives (DOGGDN and GDOGGDN) of the present invention, in which the 6-position of the glucose residue has been converted to deoxy, are 5 to 9 times higher in their inhibitory activity against HPA and HSA than GGDN in which 6-position of the glucose residue is unmodified. Therefore, it will be understood that the maltoligosaccharide derivatives of the present invention having such a strong inhibitory action against HPA and HSA can provide α-amylase inhibitors by using these derivatives as active principle.

EXAMPLE 4
(Anti-Diabetic Activity of α-Amylase Inhibitors)
(1) Test Animals

Commercially available healthy mice [Crj:CD-1 (ICR) available from Japan Charles River Co., Ltd.

(2) Test Method

A solution of DOGGDN and corn starch (used as carbohydrate) in sterilized distilled water was forcibly administered orally to the administration groups of mice (each group consisting of 5 mice) which had been left unfed for 20 hours. To the administration groups, DOGGDN was given in amounts of 10 mg, 5 mg and 1 mg with 2,000 mg of corn starch per kg of body weight. To the control groups, the same procedure as described above was applied except that no DOGGDN was given.

Blood was collected from the orbital veniplex of each mouse just before administration and after the lapse of 0.5 hour, 1.0 hour, 1.5 hours, 2.0 hours, 3.0 hours and 4.0 hours after administration, and the concentration of glucose in the blood [blood glucose level (mg/dl)] was measured to examine the inhibitory effect against rise of blood glucose level after intake of corn starch, i.e. the anti-diabetic action. Results are shown in FIG. 1. The inhibitory effect against rise of blood sugar level was judged by the t-test. The glucose concentration in the blood was determined using a blood glucose level analyzer "ANTSENSE" [mfd. by Bayer Sankyo Co., Ltd.]. In FIG. 1, ● denotes control group, ■ denotes DOGGDN group (1 mg/Kg), ▲ denotes DOGGDN group (5 mg/Kg), ◆ denotes DOGGDN group (10 mg/Kg), and * indicates P<0.05,  indicates P<0.01, and * indicates P<0.001.

As is seen from FIG. 1, in the groups where DOGGDN, a derivative of the present invention, was administered, the rise of blood glucose level was reduced significantly as compared with the control group, which indicates that DOGGDN is effective as a prophylactic or therapeutic agent for diabetes. In the observation of defecation of each mouse after administration, no side effects such as diarrhea or loose passage in the administration groups was detected.

EXAMPLE 5

Lyophilized Powdery α-amylse Inhibitor 2.4 g of DOGGDN was dissolved in 10 ml of physiological saline, then filtered aseptically through a membrane filter. The filtrate was placed 0.1 ml each in the sterilized glass containers with the containers stoppered, and lyophilized to produce a powdery α-amylase inhibitor

EXAMPLE 6

Oral Tablet

The following components (1) to (4) were prepared:

| | | |
|---|---|---|
| (1) DOGGDN | 6 g | |
| (2) Mannitol | 20 g | |
| (3) Potato starch | 47 g | |
| (4) Magnesium stearate | 3 g | |

The above (1) and (2) were mixed, to which (3) was added as a 10% starch paste and the mixture was granulated, passed through a No. 60 mesh (B.S.) sieve, and then further screened by a No. 16 mesh (B.S.) sieve. The formed granules were mixed with (4) and compacted into tablets with a diameter of 10 mm and a weight of 500 mg per tablet by a tablet machine, thus producing a prophylactic or therapeutic agent (oral tablet) for hyperglycemia or diabetes.

EXAMPLE 7

Capsule 5 g of GDOGGDN, 5 g of potato starch, 5 g of lactose and 1 g of crystalline cellulose were mixed well and packed in the capsules to prepare a capsuled prophylactic or therapeutic agent for hyperglycemia or diabetes of the present invention containing 50 mg of a derivative of the present invention per capsule as active principle.

EXAMPLE 8

Liquid Medicine for Internal Use 0.1 ml of benzoic acid (45% v/v ethanol) and purified water were added to 1 g of DOGGDN to make the total amount 10 ml, thereby preparing a prophylactic or therapeutic agent (liquid medicine for internal use) for hyperglycemia or diabetes of the present invention.

EXAMPLE 9

Injection 0.5 g of sterilized DOGGDN was dissolved in distilled water for injection to make the total amount 30 ml and the liquid was contained in the ampuls at a rate of 3.0 ml per ampul, thereby preparing an injection for the prevention or treatment of hyperglycemia or diabetes of the present invention.

EFFECT OF THE INVENTION

The maltoligosaccharide derivatives of the present invention represented by the above-shown formula (1) have a strong inhibitory action against α-amylase and also produce no side effects such as diarrhea and loose passage, so that by containing these derivatives as active principle, it is possible to obtain excellent medicinal efficacy as an α-amylase inhibitor or as a prophylactic or therapeutic agent for hyperglycemia, for example, diabetes, obesity and the diseases caused thereby such as hyperlipidemia, fatty liver, autonomic trouble, arteriosclerosis and cataract, especially for diabetes.

Figure 1:
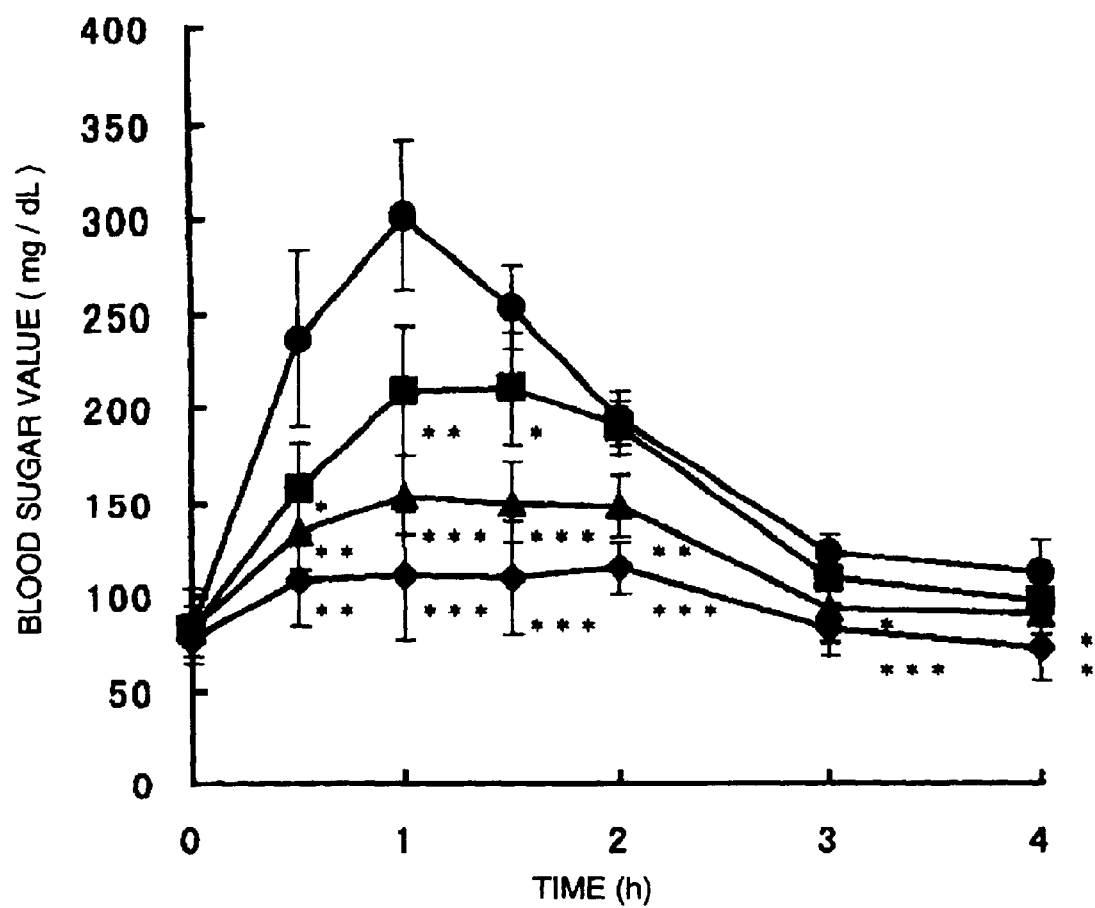
FIG. 1 show the relation between the concentration of administered DOGGDN and the lapse of time after its intake and the glucose level (mg/dl) in the blood collected from the orbital veniplex of the mice.

What is claimed is:

1. A maltoligosaccharide derivative represented by the formula:

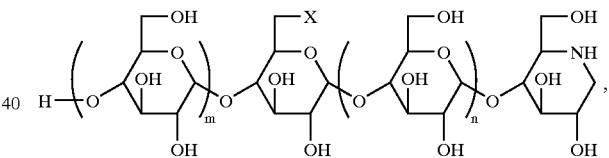

a hydrate thereof, or a physiologically acceptable salt thereof, wherein n is an integer from 0 to 2; m is an integer from 0 to 2; and X represents a hydrogen atom or a halogen atom.

2. The maltoligosaccharide derivative of claim 1 wherein X is a hydrogen atom.

3. The maltoligosaccharide derivative of claim 1 wherein n is 1, m is an integer from 0 to 1 and X is a hydrogen atom.

4. An α-amylase inhibitor preparation comprising (1) as its active principle a maltoligosaccharide derivative of claim 1 and (2) a compounding agent selected from the group consisting of an excipient, a lubricant, a diluent, a stabilizer, a pH adjuster, an antiseptic, a sweetener, an aromatic, a taste corrective, a colorant, a preservative, an emulsifier, a binder, and a basic material.

5. The α-amylase inhibitor preparation of claim 4 wherein X is a hydrogen atom.

6. The α-amylase inhibitor preparation of claim 4 wherein n is 1, m is an integer from 0 to 1 and X is a hydrogen atom.

7. A method for the treatment of hyperglycemia, said method comprising administering, to a patient in need of such administration, a maltoligosaccharide derivative represented by the formula:

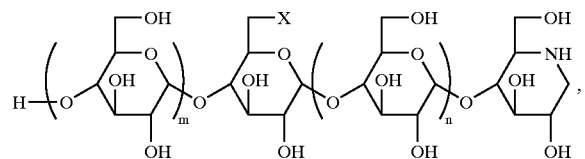
a hydrate thereof, or a physiologically acceptable salt thereof, wherein n is an integer from 0 to 2; m is an integer from 0 to 2; and X represents a hydrogen atom or a halogen atom.
8. The method of claim 7, wherein X is a hydrogen atom.
9. The method of claim 7, wherein n is 1, m is an integer from 0 to 1 and X is a hydrogen atom.
* * * * *

UNITED STATES PATENT AND TRADEMARK OFFICE
CERTIFICATE OF CORRECTION

PATENT NO. : 6,939,858,B2
DATED : September 6, 2005
INVENTOR(S) : Riichiro Uchida et al.

It is certified that error appears in the above-identified patent and that said Letters Patent is hereby corrected as shown below:

Title page,
Item [75], Inventors, insert the following:
-- Yukihiko Iwai, Noda (JP);
   Takao Someya, Noda (JP);
   Koichiro Tobe, Noda (JP) --.

Signed and Sealed this

Twenty-seventh Day of December, 2005

JON W. DUDAS
*Director of the United States Patent and Trademark Office*